US00PP22884P2

(12) United States Plant Patent

Sakazaki

(10) Patent No.: US PP22,884 P2

(45) Date of Patent: Jul. 24, 2012

(54) *PETUNIA* PLANT NAMED 'USTUN34803'

(50) Latin Name: *Petunia×hybrida*
Varietal Denomination: USTUN34803

(75) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 205 days.

(21) Appl. No.: 12/802,248

(22) Filed: Jun. 1, 2010

(51) Int. Cl.
*A01H 5/00* (2006.01)

(52) U.S. Cl. ..... Plt./356.21

(58) Field of Classification Search ..... Plt./356, Plt./356.21
See application file for complete search history.

*Primary Examiner* — Susan McCormick Ewoldt

(74) *Attorney, Agent, or Firm* — C. A. Whealy

(57) ABSTRACT

A new and distinct cultivar of *Petunia* plant named 'USTUN34803', characterized by its outwardly spreading and low mounding plant habit; freely branching and vigorous growth habit; early and freely flowering habit; small red purple-colored flowers; and good garden performance.

1 Drawing Sheet

Botanical designation: *Petunia×hybrida.*
Cultivar denomination: 'USTUN34803'.

BACKGROUND OF THE INVENTION

The present invention relates to a new and distinct cultivar of *Petunia* plant, botanically known as *Petunia×hybrida* and hereinafter referred to by the name 'USTUN34803'.

The new *Petunia* plant is a product of a planned breeding program conducted by the Inventor in Hikone, Shiga, Japan and Bonsall, Calif. The objective of the breeding program is to create new *Petunia* plants with compact plant habit, freely branching growth habit, early flowering, attractive small flowers and good summer performance.

The new *Petunia* plant originated from a cross-pollination made by the Inventor on May 15, 2007 in Hikone, Shiga, Japan of *Petunia×hybrida* 'USTUNI8902', disclosed in U.S. Plant Pat. No. 17,895, as the female, or seed, parent with a proprietary seedling selection of *Petunia×hybrida* identified as code number 07 red 1, not patented, as the male, or pollen, parent. The new *Petunia* plant was discovered and selected by the Inventor as a single flowering plant within the progeny of the stated cross-pollination in a controlled environment in Bonsall, Calif. on May 21, 2008.

Asexual reproduction of the new *Petunia* plant by vegetative cuttings in a controlled greenhouse environment in Bonsall, Calif. since May 23, 2008, has shown that the unique features of this new *Petunia* plant are stable and reproduced true to type in successive generations.

SUMMARY OF THE INVENTION

Plants of the new *Petunia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'USTUN34803'. These characteristics in combination distinguish 'USTUN34803' as a new and distinct cultivar of *Petunia* plant:

1. Outwardly spreading and low mounding plant habit.
2. Freely branching and vigorous growth habit.
3. Early and freely flowering habit.
4. Small red purple-colored flowers.
5. Good garden performance.

In side-by-side comparisons conducted in Bonsall, Calif., plants of the new *Petunia* differ from plants of the female parent, 'USTUNI8902', in the following characteristics:

1. Plants of the new *Petunia* are more compact than plants of 'USTUNI8902'.
2. Plants of the new *Petunia* have smaller flowers than plants of 'USTUNI8902'.
3. Plants of the new *Petunia* and 'USTUNI8902' differ in flower color as plants of 'USTUNI8902' have fuchsia-colored flowers.

In side-by-side comparisons conducted in Bonsall, Calif., plants of the new *Petunia* differ from plants of the male parent selection in the following characteristics:

1. Plants of the new *Petunia* are more compact than plants of the male parent selection.
2. Plants of the new *Petunia* and the male parent selection differ in flower color as plants of the male parent selection have red-colored flowers.

Plants of the new *Petunia* can be compared to plants of 'USTUNI6001', disclosed in U.S. Plant Pat. No. 17,730. In side-by-side comparisons conducted in Bonsall, Calif., plants of the new *Petunia* differed from plants of 'USTUNI6001' in the following characteristics:

1. Plants of the new *Petunia* were more compact than and not as vigorous as plants of 'USTUNI6001'.
2. Plants of the new *Petunia* had smaller flowers than plants of 'USTUNI6001'.
3. Plants of the new *Petunia* and 'USTUNI6001' differed in flower color as plants of 'USTUNI6001' had bright pink-colored flowers.

Plants of the new *Petunia* can also be compared to plants of 'Conglow', disclosed in U.S. Plant Pat. No. 13,545. In side-by-side comparisons, plants of the new *Petunia* differed from plants of 'Conglow' in the following characteristics:

1. Plants of the new *Petunia* were not as trailing as plants of 'Conglow'.

2. Plants of the new *Petunia* flowered earlier than plants of 'Conglow'.
3. Plants of the new *Petunia* had smaller flowers than plants of 'Conglow'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the bottom of the sheet comprises a side perspective view of a typical plant of 'USTUN34803' grown in a container.

The photograph at the top of the sheet is a close-up view of a typical flowering plant of 'USTUN34803'.

DETAILED BOTANICAL DESCRIPTION

The aforementioned photographs and following observations, measurements and values describe plants grown during the spring in 15-cm containers in an outdoor nursery in Bonsall, Calif. During the production of the plants, day temperatures ranged from 18° C. to 24° C., night temperatures ranged from 5° C. to 8° C. and light levels ranged from 7,000 to 10,000 foot-candles. Plants were pinched one time and were ten weeks old when the photographs and description were taken. In the following description, color references are made to The Royal Horticultural Society Colour Chart, 2007 Edition, except where general terms of ordinary dictionary significance are used.

Botanical classification: *Petunia×hybrida* 'USTUN34803'.

Parentage:

*Female, or seed, parent.*—*Petunia×hybrida* 'USTUNI8902', disclosed in U.S. Plant Pat. No. 17,895.

*Male, or pollen, parent.*—Proprietary seedling selection of *Petunia×hybrida* identified as code number 07 red 1, not patented.

Propagation:

*Type.*—Terminal vegetative cuttings.

*Time to initiate roots, summer.*—About three days at temperatures ranging from 17° C. to 29° C.

*Time to initiate roots, winter.*—About four days at temperatures ranging from 17° C. to 21° C.

*Time to produce a rooted plant, summer.*—About 15 days at temperatures ranging from 17° C. to 29° C.

*Time to produce a rooted plant, winter.*—About 20 days at temperatures ranging from 17° C. to 21° C.

*Root description.*—Medium in thickness, fibrous; white in color.

*Rooting habit.*—Freely branching; moderately dense.

Plant description:

*Plant and growth habit.*—Annual flowering plant; outwardly spreading and low mounding plant habit; vigorous growth habit; freely branching habit with about four to five primary lateral branches and numerous secondary lateral branches per plant; pinching enhances development of lateral branches; dense and bushy habit.

*Plant height.*—About 15 cm.

*Plant diameter* (*area of spread*).—About 52 cm.

*Lateral branches.*—Length: About 30 cm. Diameter: About 2 mm. Internode length: About 1 cm to 3 cm. Strength: Strong. Texture: Pubescent; viscid, glandular. Color: Close to 144A.

Foliage description:

*Arrangement.*—Alternate before flowering; opposite after flowers develop; simple.

*Length.*—About 4 cm.

*Width.*—About 1.4 cm.

*Shape.*—Elliptical to lanceolate.

*Apex.*—Acute.

*Base.*—Attenuate.

*Margin.*—Entire.

*Texture, upper and lower surfaces.*—Pubescent; viscid, glandular.

*Venation pattern.*—Pinnate, arcuate.

*Color.*—Developing leaves, upper surface: Close to 137A. Developing leaves, lower surface: Close to 137B. Fully expanded leaves, upper surface: Close to 137A; venation, close to 146B. Fully expanded leaves, lower surface: Close to 147B; venation, close to 146C.

*Petioles.*—Length: About 5 mm. Diameter: About 1.5 mm. Texture, upper and lower surfaces: Pubescent; glandular. Color, upper surface: Close to 146B. Color, lower surface: Close to 146C.

Flower description:

*Flower type and habit.*—Single axillary salverform flowers; flowers face mostly upward or outward; freely flowering habit, about 46 flower buds and open flowers per lateral branch.

*Natural flowering season.*—Long day responsive; long flowering period, plants flower from early spring until frost in the autumn, flowering continuous during this period; early flowering habit, plants begin flowering about six weeks after planting.

*Flower longevity on the plant.*—About three to five days; flowers persistent.

*Fragrance.*—Floral, sweet.

*Flower size.*—Diameter: About 3 cm to 3.2 cm. Depth (height): About 3 cm. Tube length: About 2.2 cm. Throat diameter, distal end: About 7 mm. Tube diameter, proximal end: About 2.5 mm.

*Flower buds.*—Length: About 2.7 cm. Diameter: About 5 mm. Shape: Elongated oblong. Color: Close to 201C.

*Petals.*—Quantity/arrangement: About five petals fused in a single whorl, funnelform. Petal lobe length (from throat): About 1.3 cm. Petal lobe width: About 1.4 cm. Petal lobe shape: Roughly fan-shaped. Petal lobe apex: Acute or slightly mucronate. Petal lobe margin: Entire. Petal lobe texture, upper and lower surfaces: Smooth, glabrous. Throat texture: Smooth, glabrous. Tube texture: Pubescent. Color: When opening, upper surface: Close to 70A. When opening, lower surface: Close to 201C to 201D. Fully opened, upper surface: Close to 71B; venation, close to 59A; color does not fade with development. Fully opened, lower surface: Close to 72C to 72D; venation, close to 191C; color does not fade with development. Flower throat: Close to 59C; venation, close to N79A. Flower tube (outside): Close to 59A to 59B; venation, close to 197B.

*Sepals.*—Arrangement/appearance: Single whorl of five sepals fused at base, star-shaped calyx. Length: About 1 cm. Width: About 1.5 mm. Shape: Lanceolate.

Apex: Acute to rounded. Margin: Entire. Texture, upper and lower surfaces: Pubescent. Color, upper surface: Close to 144A. Color, lower surface: Close to 146B.

*Peduncles*.—Length: About 3.7 cm. Width: About 1 mm. Angle: About 45° to 60° from the stem axis. Strength: Moderately strong. Texture: Pubescent. Color: Close to 146C.

*Reproductive organs*.—Stamens: Quantity per flower: Five. Filament length: About 1.2 cm. Filament color: Close to 157A. Anther shape: Oval. Anther length: About 2 mm. Anther color: Close to 198C. Pollen amount: Scarce. Pollen color: Close to 198A. Pistils: Quantity per flower: One. Pistil length: About 1.7 cm. Style length: About 1.2 cm. Style color: Close to 145C. Stigma shape: Rounded anvil-shaped. Stigma color: Close to 146A. Ovary color: Close to 145A.

*Seed/fruit*.—Seed and/or fruit production has not been observed.

Pathogen/pest resistance: Plants of the new *Petunia* have not been noted to be resistant to pathogens or pests common to *Petunia*.

Garden performance: Plants of the new *Petunia* have been observed to have good garden and summer performance and have been observed to tolerate rain, wind and temperatures ranging from about 1° C. to about 40° C.

It is claimed:

1. A new and distinct *Petunia* plant named 'USTUN34803' as illustrated and described.

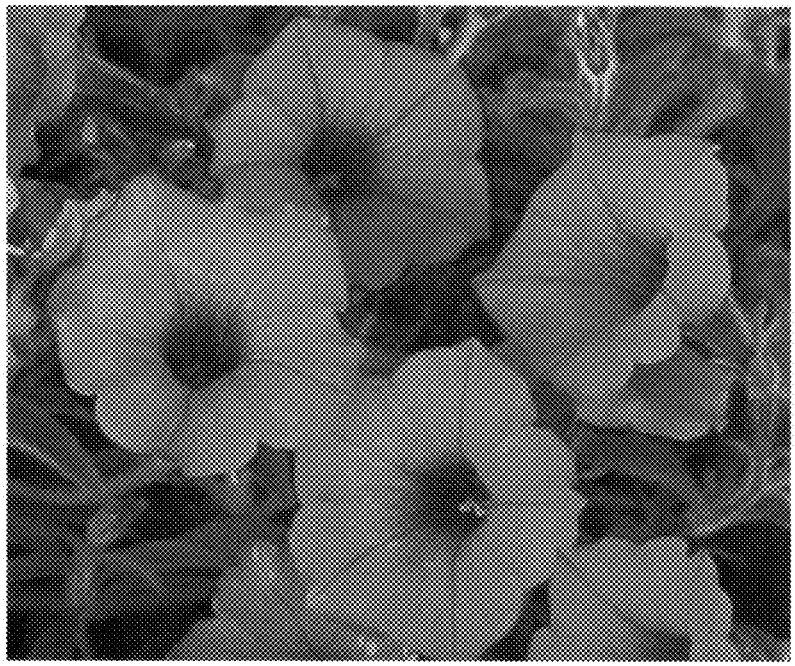
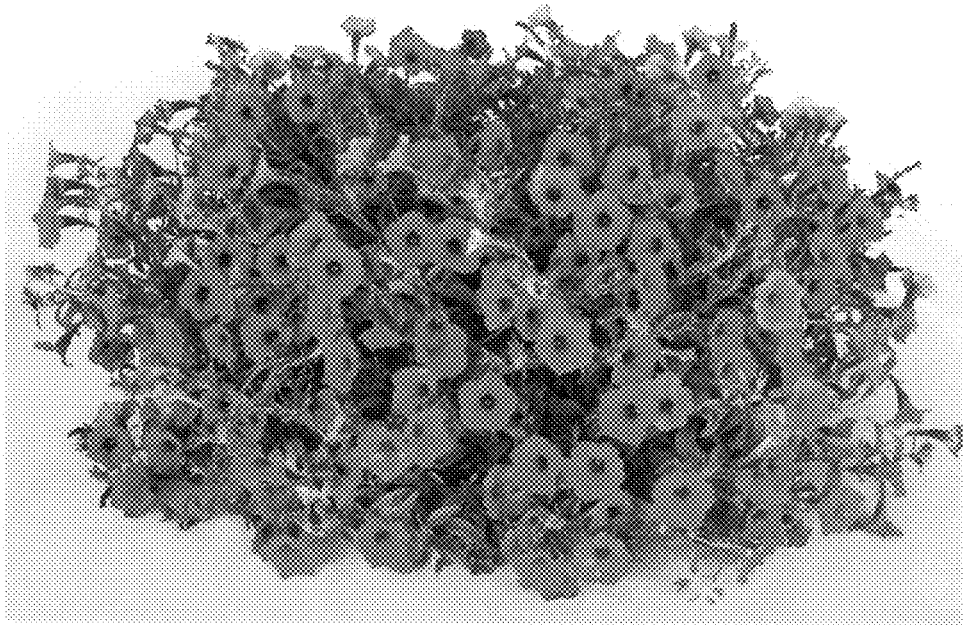

* * * * *